(12) United States Patent
Kornet et al.

(10) Patent No.: US 12,558,546 B2
(45) Date of Patent: Feb. 24, 2026

(54) DORSAL ROOT GANGLION STIMULATION IN INFLUENCING ORGAN FUNCTION

(71) Applicant: Medtronic, Inc., Minneapolis, MN (US)

(72) Inventors: Lilian Kornet, Berg en Terblijt (NL); Richard Cornelussen, Maastricht (NL); Mirko De Melis, Maastricht (NL); Berthold Stegemann, Kassel (DE); Jules Hamers, Munich (DE)

(73) Assignee: Medtronic, Inc., Minneapolis, MN (US)

( * ) Notice: Subject to any disclaimer, the term of this patent is extended or adjusted under 35 U.S.C. 154(b) by 791 days.

(21) Appl. No.: 17/382,743

(22) Filed: Jul. 22, 2021

(65) Prior Publication Data

US 2022/0032058 A1 Feb. 3, 2022

Related U.S. Application Data

(60) Provisional application No. 63/058,994, filed on Jul. 30, 2020.

(51) Int. Cl.
A61N 1/36 (2006.01)

(52) U.S. Cl.
CPC ..... A61N 1/36057 (2013.01); A61N 1/36062 (2017.08); A61N 1/36139 (2013.01)

(58) Field of Classification Search
CPC ........... A61N 1/36057; A61N 1/36062; A61N 1/36139; A61N 1/0551; A61N 1/3605; A61N 5/0601; A61N 1/36135; A61N 1/36007; A61N 1/36017; A61N 1/0456; A61N 1/205; A61N 1/0492; A61B 2018/00511; A61B 5/14532
See application file for complete search history.

(56) References Cited

U.S. PATENT DOCUMENTS

| | | | |
|---|---|---|---|
| 8,868,188 B2 | 10/2014 | Hershey | |
| 9,174,065 B2 | 11/2015 | Gertner | |
| 2003/0216792 A1* | 11/2003 | Levin | A61M 5/1723 |
| | | | 607/48 |
| 2008/0119907 A1 | 5/2008 | Stahmann | |
| 2010/0249865 A1 | 9/2010 | Zhang et al. | |

(Continued)

FOREIGN PATENT DOCUMENTS

| | | |
|---|---|---|
| WO | 2012/027734 | 3/2012 |
| WO | 2012/083259 | 6/2012 |

OTHER PUBLICATIONS

Huang, Te & Kecman, Vojislav & Kopriva, Ivica. (2006). Kernel Based Algorithms for Mining Huge Data Sets: Supervised, Semi-Supervised, and Unsupervised Learning. 10.1007/3-540-31689-2. (Year: 2006).*

(Continued)

*Primary Examiner* — Benjamin J Klein
*Assistant Examiner* — Daniel Tehrani
(74) *Attorney, Agent, or Firm* — Mueting Raasch Group

(57) ABSTRACT

Systems and methods are directed to influencing organ function by stimulating the dorsal root ganglion. Systems include at least one electrode to deliver electrical stimulation to the dorsal root ganglion to activate afferent nerves innervating at least one organ, and computing apparatus comprising one or more processors operably coupled to the at least one electrode to control the electrical stimulation.

23 Claims, 6 Drawing Sheets

(56)　　　　　References Cited

U.S. PATENT DOCUMENTS

| | | | |
|---|---|---|---|
| 2012/0277836 A1* | 11/2012 | Knoblich | A61N 1/36017 |
| | | | 607/117 |
| 2014/0114215 A1 | 4/2014 | Melder et al. | |
| 2014/0277250 A1* | 9/2014 | Su | A61N 1/36007 |
| | | | 607/40 |
| 2015/0142074 A1* | 5/2015 | Bar-Yoseph | A61N 1/0558 |
| | | | 607/40 |
| 2017/0189684 A1 | 7/2017 | Weber et al. | |
| 2018/0126172 A1 | 5/2018 | Sarkar et al. | |
| 2018/0177549 A1 | 6/2018 | Harrington et al. | |
| 2019/0223935 A1 | 7/2019 | Melder | |

OTHER PUBLICATIONS

Sata, Yusuke & Head, Geoffrey & Denton, Kate & May, Clive & Schlaich, Markus. (2018). Role of the Sympathetic Nervous System and Its Modulation in Renal Hypertension. Frontiers in Medicine. 5. 82. 10.3389/fmed.2018.00082. (Year: 2018).*

Akopian et al., "A tetrodotoxin-resistant voltage-gated sodium channel expressed by sensory neurons", Nature. 1996;379:257.

Aronson et al., "Elevated blood urea nitrogen level as a predictor of mortality in patients admitted for decompensated heart failure", The American Journal of Medicine. 2004;116(7):466-73.

Benjamin et al., "Heart Disease and Stroke Statistics—2018 Update: A Report From the American Heart Association" Circulation, 2018;137(12):e67-e492.

Berne et al., "Effects of Antihypertensive Treatment on Insulin Sensitivity With Special Reference to ACE Inhibitors", Diabetes Care. 1991;14(4):39-47.

Bhatt et al., "A Controlled Trial of Renal Denervation for Resistant Hypertension", New England Journal of Medicine. 2014;370(15):1393-401.

Ditting et al., "Do distinct populations of dorsal root ganglion neurons account for the sensory peptidergic innervation of the kidney?", American Journal of Physiology—Renal Physiology. 2009;297(5):F1427-F34.

Ellison, "Diuretic Treatment in Heart Failure", New England Journal of Medicine. 2017;377(1):1964-75.

Filippatos et al., "Prognostic Value of Blood Urea Nitrogen in Patients Hospitalized With Worsening Heart Failure: Insights From the Acute and Chronic Therapeutic Impact of a Vasopressin Antagonist in Chronic Heart Failure (ACTIV in CHF) Study", Journal of Cardiac Failure. 2007;13(5):360-4.

Fonarow et al., "Temporal trends in clinical characteristics, treatments, and outcomes for heart failure hospitalizations, 2002 to 2004: findings from Acute Decompensated Heart Failure National Registry (ADHERE)", American Heart Journal. 153(6):1021-8.

Koga et al., "Selective activation of primary afferent fibers evaluated by sine-wave electrical stimulation", Molecular Pain. 2005;1:13.

Liem, "Stimulation of the Dorsal Root Ganglion for the Treatment of Chronic Pain", Nieuwegein, 2015.

Nishi et al., "The crosstalk between the kidney and the central nervous system: the role of the renal nerves in blood pressure regulation", Experimental Physiology. 2015;100(5):479-84.

Pourmoghaddas et al., "One year follow-up effect of renal sympathetic denervation in patients with resistant hypertension", ARYA Atherosclerosis. 2016;12(2):109-13.

Shishehbor et al., "Renal denervation: What happened, and why?", 2017. 681-6 p.

Taniguchi et al., "Abdominal admittance helps to predict the amount of fluid accumulation in patients with acute heart failure syndromes", Journal of Cardiology. 2016;67(4):352-7.

Xu et al., "Activation of afferent renal nerves modulates RVLM-projecting PVN neurons", American Journal of Physiology—Heart and Circulatory Physiology. 2015;308(9):H1103-H11.

International Search Report and Written Opinion from PCT Application No. PCT/US2021/042922 dated Oct. 27, 2021, 14 pages.

Salman, "Cardiovascular Autonomic Dysfunction in Chronic Kidney Disease: a Comprehensive Review", Current Hypertension Reports, vol. 17, No. 8, Jun. 2015, pp. 1-20.

International Search Report and Written Opinion from PCT Application No. PCT/US2021/042925 dated Oct. 27, 2021, 14 pages.

* cited by examiner

DORSAL ROOT GANGLION STIMULATION IN INFLUENCING ORGAN FUNCTION

RELATED APPLICATIONS

This application claims the benefit under 35 U.S.C. § 119 of U.S. Provisional Application Ser. No. 63/058,994, filed Jul. 30, 2020, which is incorporated herein by reference in its entirety.

BACKGROUND

The present disclosure relates to influencing organ function; and, more particularly, influencing the functioning of organs, such as the kidneys, through stimulating the dorsal root ganglion.

Nerve tissue contains both efferent fibers and afferent fibers. Electrical signals propagate from the central nervous system to tissue/organs along efferent fibers while electrical signals propagate from tissues/organs to the central nervous system along afferent fibers. Applying electrical signals to nerve fibers (e.g., afferent fibers) proximate the dorsal root ganglion can be used to innervate targeted organ functions to alleviate patient discomfort or as at least a part of patient therapies.

SUMMARY

The disclosure herein relates generally to a system comprising at least one electrode and computing apparatus comprising one or more processors that is operably coupled to the at least one electrode. The at least one electrode delivers electrical stimulation to a patient's dorsal root ganglion (DRG) to activate renal afferent and/or other nerves innervating at least one of the patient's kidneys. The computing apparatus is configured to control the electrical stimulation delivered by the at least one electrode to the DRG to inhibit activation of renal efferent nerves innervating the at least one of the patient's kidneys to promote diuresis.

In certain embodiments one or more electrodes are configured to deliver electrical stimulation to at least one, or both, of the left and right DRG of at least one of the T10 to L1 vertebrae of the patient to activate renal afferent nerves innervating at least one of the patient's kidneys. The one or more electrodes may be implanted in the patient's body or positioned external to the patient's body, e.g., on, or adhered to, the patient's skin.

In certain embodiments, the electrical stimulation delivered by the at least one electrode is controlled based on at least one of a predetermined schedule, an activity sensor, and a sensed position of the patient's body. In further embodiments, the electrical stimulation is controlled in response to one or more detected physiological parameters including at least one of a patient's creatinine level, a patient's blood urea nitrogen level, a patient's respiration rate, a patient's abdominal fluid content, a patient's thoracic fluid content, and a patient's capillary wedge pressure. The electrical stimulation may be controlled with respect to a threshold including one or more of a rate of change passing a predetermined, individualized threshold, a sensed parameter being equal to or greater than a threshold, and a combination of detected parameters meeting or exceeding a threshold. In certain embodiments, the one or more parameters provide input to a self-learning algorithm and may be used to determine a threshold to initiate stimulating based on one or more parameters including a subset of additional parameters.

Additional embodiments are directed to a system comprising at least one electrode to deliver electrical stimulation to a patient's DRG to activate afferent nerves innervating at least one of the patient's organs. The system further comprises computing apparatus comprising one or more processors and operably coupled to the at least one electrode and configured to control the electrical stimulation delivered by the at least one electrode to the DRG to inhibit efferent nerves innervating the at least one of the patient's organs.

Further embodiments are directed to a method comprising determining at least one physical parameter of a patient and comparing the at least one physical parameter with a selected threshold for the parameter. When the physical parameter meets or exceeds the selected threshold, a dorsal root ganglion of the patient is stimulated to influence at least one function of an organ of the patient.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1A:
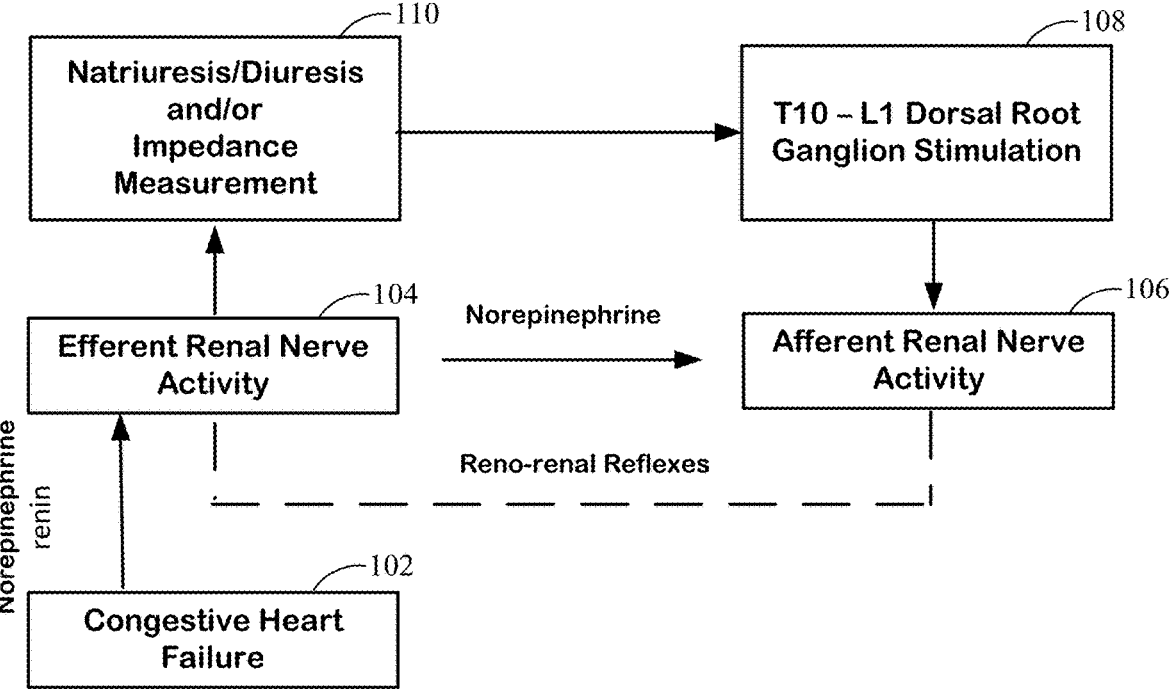
FIG. 1A is a diagram illustrating electrical stimulation of a patient's reno-renal reflex, according to embodiments discussed herein.

In the following detailed description of illustrative embodiments, reference is made to the accompanying figures which form a part hereof, and in which are shown, by way of illustration, specific embodiments which may be practiced. It is to be understood that other embodiments may be utilized and structural changes may be made without departing from (e.g., still falling within) the scope of this disclosure.

Exemplary methods, devices, and systems are described with reference to FIGS. 1A-5. Elements or processes from one embodiment can be used in combination with elements or processes of the other embodiments, and the possible embodiments of such methods, devices, and systems using combinations of features set forth herein is not limited to the specific embodiments shown in the figures described herein. Further, it will be recognized that the embodiments described herein may include many elements that are not necessarily shown to scale. Still further, it will be recognized that timing of the process operations and/or the size and shape of various elements herein may be modified but still fall within the scope of the present disclosure, although certain timing, one or more shapes and/or sizes, or types of elements, may be advantageous over others.

During heart failure episodes, such as acute decompensated heart failure, kidney flow and function are overactivated, which may lead to less diuresis and a higher blood volume. Further, an already weakened heart, by heart failure insults, cannot process an increased blood volume, which may lead to congestion and fluid movement into nearby organs, causing dyspnoe and oedema of one or more organs.

Unfortunately, certain forms of treatment to increase diuresis may become hazardous when used for extended periods of time. For example, the first line of treatment against congestive heart failure may frequently be "loop diuretics." Loop diuretics inhibit the $Na^+/K^+/2Cl^-$ co-transport in the ascending part of Henle's loop in nephrons, by which the sodium concentration in the blood decreases and reduces the reabsorption of water, which may result in increased urine production. However, when chronically used, loop diuretics may be toxic for the kidney(s) and can lead to structural changes of a kidney such as hypertrophy of the epithelial cells in the distal tubules, which enhance distal reabsorption of sodium and limit sodium excretion and diuresis. The need to increase the dosage of loop diuretic medication over time may be exacerbated because the use of loop diuretics lowers the dose-response curve. In addition, loop diuretics might interact with heart failure medication and may be less well absorbed if the stomach lining is damaged as often occurs in heart failure patients, making loop diuretics less effective. Moreover, the chronic intake of medication can negatively affect a patient's psychological health by continually reminding them of their health concerns. Further, poor compliance of taking loop diuretics by patients may also be an issue.

An alternative treatment described herein, utilizes a negative feedback loop referred to as the reno-renal reflex. In healthy patients, the reno-renal reflex is activated by the renal efferent nerves, which stimulate water retention thereby increasing blood volume. Activation of the reno-renal reflex ensures a continuous retention of water by the kidney. The reflex involves the afferent nerves activating to inhibit the renal efferent nerves resulting in diuresis. However, in patients with congestive heart failure and acute decompensated heart failure, the activation of the renal afferent nerves may be impaired. Therefore, efferent nerves, and resultingly, water reabsorption, may not be suppressed.

Alternative treatments, described in various embodiments herein, activate the renal nerves (e.g., afferent nerves) through electrical stimulation to mimic their electrical activation signals in their corresponding dorsal root ganglions (DRGs). This is illustrated in the diagram of FIG. 1A. When patients have congestive (or acute decompensated) heart failure 102, such patients may experience increased norepinephrine in the body, which reduces natriuresis/diuresis 110. This, in turn, leads to treatment with loop diuretics, which, in addition to the increase in norepinephrine, impairs the activation of the renal afferent nerves 106, which further suppresses the reno-renal reflexes.

As described herein, instead of treatment with loop diuretics, a patient may be treated by electrically stimulating the dorsal root ganglion of the T10 to L1 locations 108, as appropriate, to mimic the activation signals of the afferent nerves 106. This induces the reno-renal reflexes and restores, at least in part, the natural inhibition of the efferent renal nerve activity 104 to increase natriuresis/diuresis 110. In certain embodiments, physical parameters such as abdominal impedance may be measured and/or monitored 110 to determine when DRG stimulation should be administered as discussed further below.

Activating the renal nerves (e.g., afferent nerves) through electrical stimulation to mimic their electrical activation signals in their corresponding dorsal root ganglions (DRGs) may also provide an alternative therapy for other conditions, such as hypertension. When renal denervation is used to lower hypertension, a catheter is positioned in the renal arteries to ablate sympathetic nerves innervating the kidneys. This leads to an increase in renal blood flow, an increase in urinary excretion of salt and water, and a decrease in renin release from the kidney along with other central sympathetic effects to treat hypertension. However, problems associated with renal denervation include limited efficacy, limited applicability, and the possibility of unsustainability over time. For example, it is not a single nerve that needs to be denervated and the nerves are not always close to the vessel and may be closer to site branches. Also, exclusion criteria in two trials included >50% renal artery stenosis, eGFR<45 ml/min/1.73 $m^2$, and renal artery anatomy that was unsuitable for ablation. Moreover, re-innervation has been shown to occur in rats after three months and sheep after eleven months; however this has not been studied in humans.

As an alternative to using renal denervation to treat hypertension, the dorsal root ganglion(s) connected to the kidneys can be stimulated at the T10-L1 level. This therapy would also increase renal blood flow, increase urinary excretion of salt and water, and decrease renin release from the kidney along with other central sympathetic effects to treat hypertension. For example, a central sympathetic decrease would include a decrease in arterial and artery resistance decreasing afterload. Also, heart rate would be affected decreasing energy expenditure of the heart. However, there would be no incomplete targeting of nerves causing limited efficacy or concerns with re-innervation since nerves are not ablated with DRG stimulation. Instead, the reflex sending renal sensory information to the brain is interrupted, which in turn, affects kidney function. Using DRG stimulation for hypertension can also be administered to patients with arterial renal stenosis.

Figure 1B:
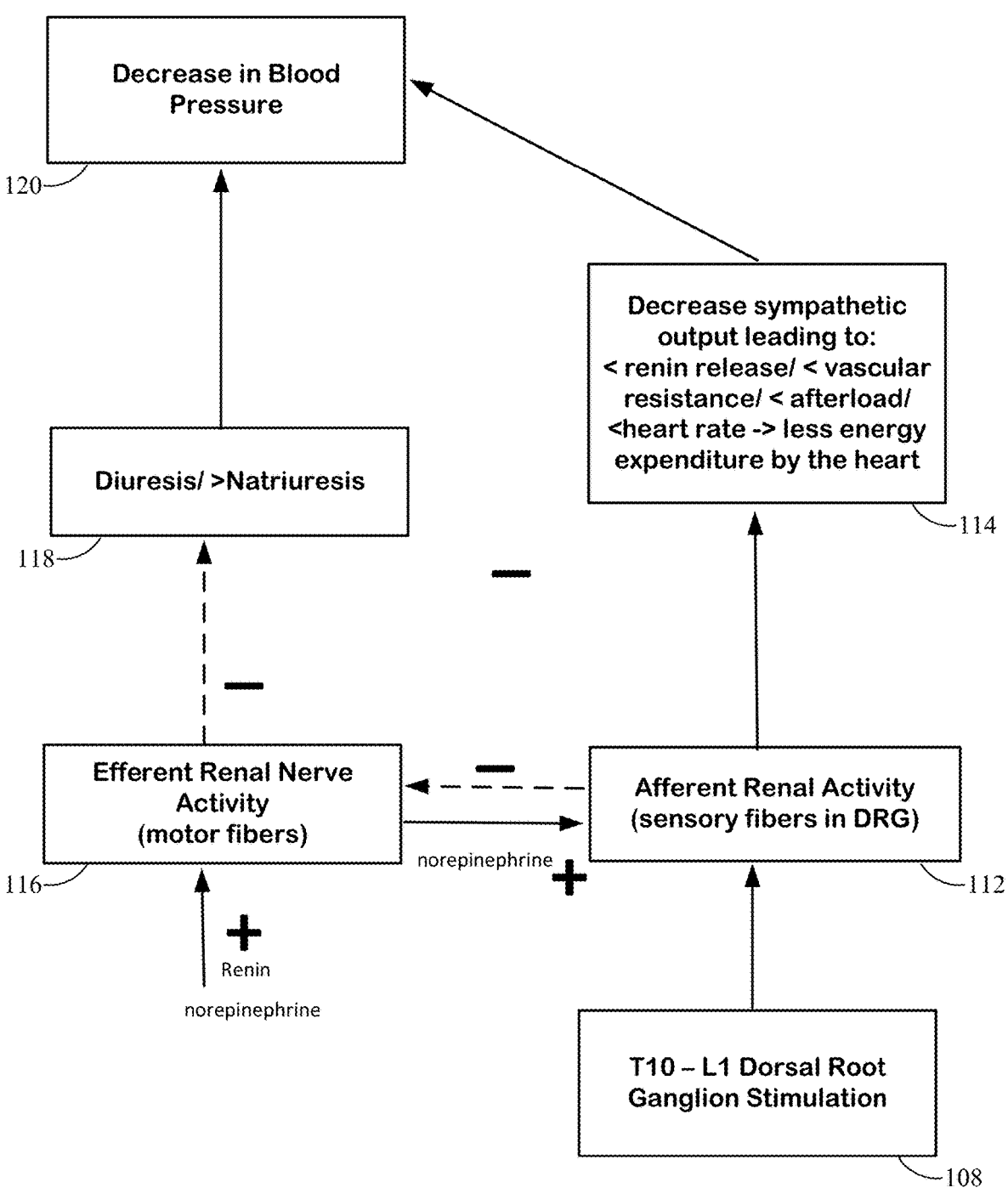
FIG. 1B is a diagram illustrating electrical stimulation of a patient's DRG to influence a decrease in blood pressure, according to embodiments discussed herein.

FIG. 1B illustrates how activating the renal nerves (e.g., afferent nerves) through electrical stimulation to mimic their electrical activation signals in their corresponding dorsal root ganglions (DRGs) can be used as a therapy for hypertension. When patients have hypertension, they may experience increased norepinephrine in the body which activates efferent renal nerves such as motor fibers and which reduces natriuresis/diuresis. Instead of treatment with renal denervation, a patient may be treated by electrically stimulating the dorsal root ganglion of the T10 to L1 locations 108, as appropriate, to mimic the activation signals of the afferent nerves 112. This induces the reno-renal reflexes and restores, at least in part, the natural inhibition of the efferent renal nerve activity 116 to increase natriuresis/diuresis 118. Activation of the afferent nerves also decreases sympathetic output leading to a decrease in renin release, a decrease in vascular resistance, a decrease in afterload, and a decrease in heart rate, leading to less energy expenditure by the heart 114. Both the decrease in sympathetic output and increase in diuresis influence a decrease in blood pressure 120, thereby lowering a patient's hypertension. In certain embodiments, physical parameters such as blood pressure and/or heart rate may be measured and/or monitored to determine when DRG stimulation should be administered as discussed further below.

Figure 2:
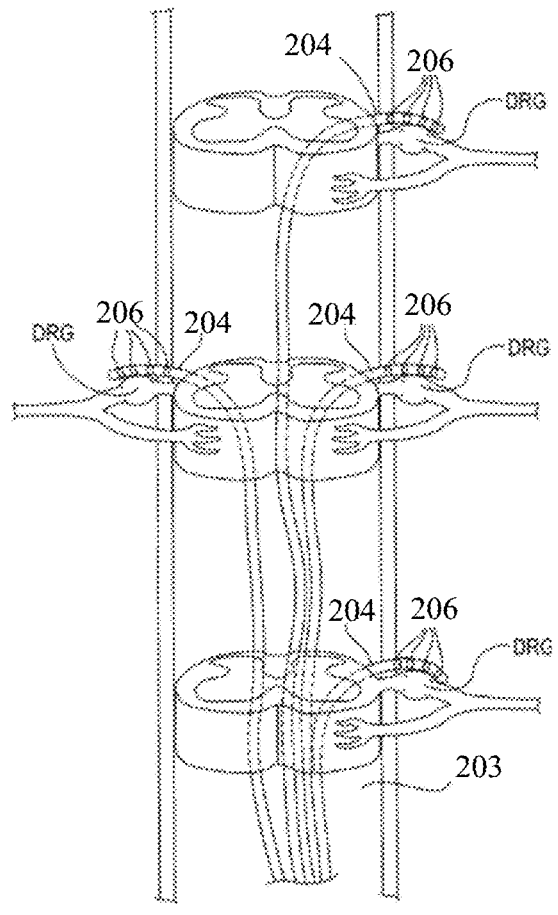
FIG. 2 is a schematic diagram of an implantable medical device (IMD) operably coupled to a patient's dorsal root ganglion, according to embodiments discussed herein.
Figure 2:
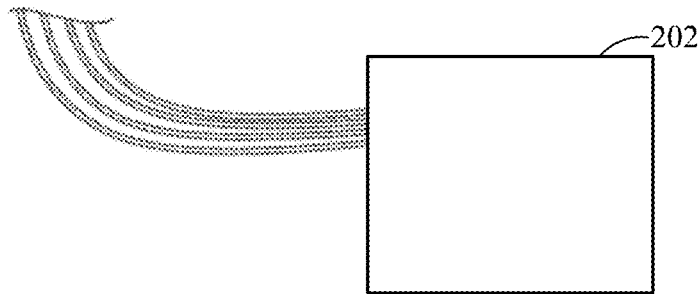
Figure 3:
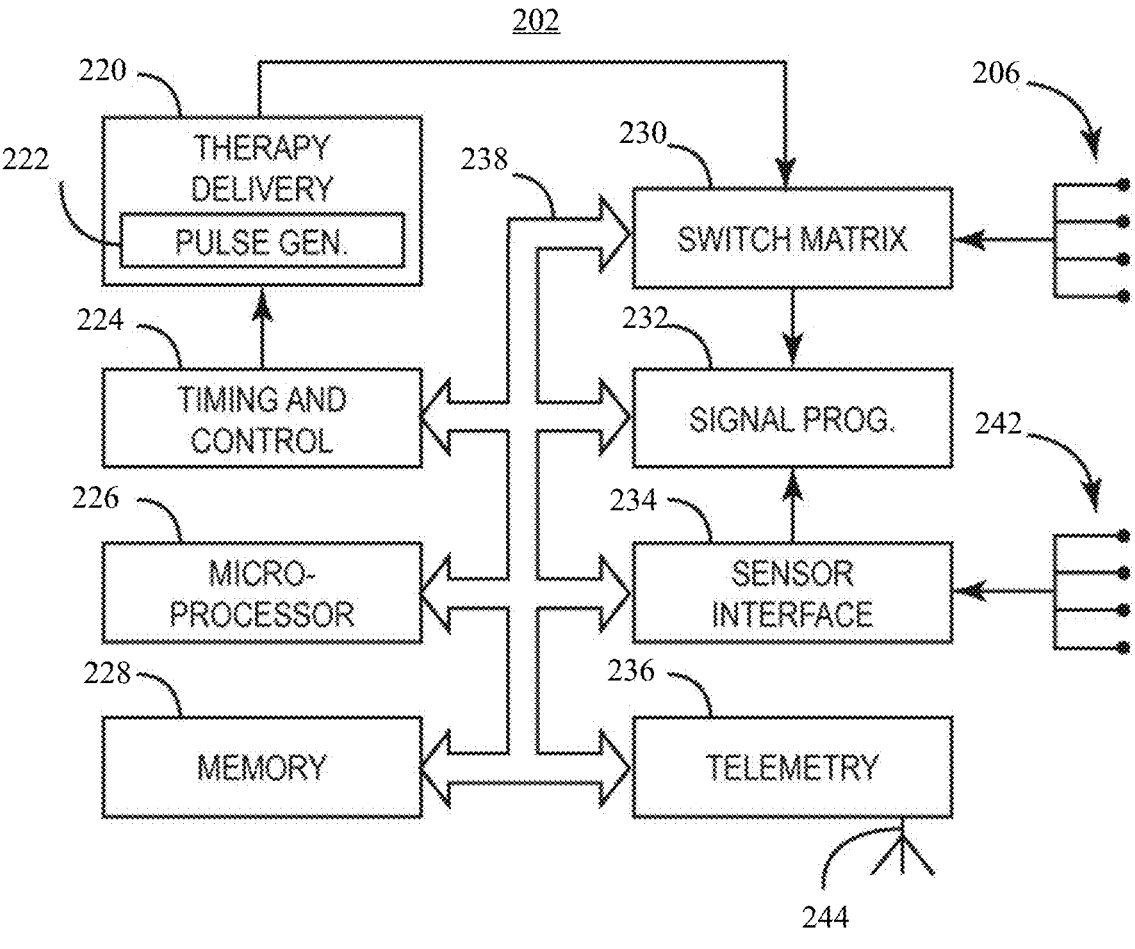
FIG. 3 is a block diagram of the IMD shown in FIG. 2.

Electrical stimulation of the patient's DRG may be controlled and administered by an implantable medical device 202 as shown in FIGS. 2-3. Although the IMD 202 depicted in FIG. 2 uses four leads 204, one, two three, or more than four leads may be used with the methods, devices, and systems described herein. Also, while each lead 204 is shown with four electrodes 206 positioned or located at the distal ends of the leads, each lead may have fewer, or more, electrodes. For example, a lead may have four to eight electrodes. Further, for example, a lead may have a single electrode or two electrodes. Each of the leads 204 may have a different number of electrodes as well.

In FIG. 2, the IMD 202 is coupled to leads 204 and the leads 204 are positioned (e.g., implanted in tissue of the patient) to stimulate a patient's dorsal root ganglions. The four leads 204 are shown as being individually advanced and positioned proximate four different DRGs along a patient's spinal column 203. The DRGs are located on three different levels, with two DRGs being stimulated on the same level. However, any number of DRGs and any combination of DRGs may be stimulated in accordance with embodiments described herein. For example, one DRG on one side of the spine may be stimulated, DRGs on opposing sides of the spine at the same level may be stimulated, DRGs at different levels on the same side of the spine may be stimulated, or DRGs on both sides of the spine together or staggered at different levels may be stimulated. When an organ is part of a pair (e.g., kidneys), the electrodes can be positioned to stimulate either organ in the pair or both organs together—simultaneously or with staggered timing. In addition, more than one lead may be positioned proximate the same DRG and/or one lead may be positioned to stimulate more than one DRG.

The electrodes 206 may have any variety of configurations or combinations designed to stimulate one or more of a patient's DRGs. As each electrode 206, and lead 204, may be independently configurable, at any given time a single lead may be stimulating, more than one lead may be stimulating, or stimulation by different leads may be staggered or overlapping. The electrodes 206 are able to selectively stimulate the DRG, due to position, electrode configuration, electrode shape, electric field shape, stimulation signal parameters, or a combination thereof. The electrodes may also be configured for sensing.

FIG. 3 is a functional block diagram of IMD 202 shown in FIG. 2. Although the IMD 202 has previously been described with respect to the dorsal root ganglions of the T10-L1 region to influence kidney function, IMD 202 may be used for monitoring and delivering therapy to the dorsal root ganglions of any spinal region to influence various other organ functions. Such organ functions may include the GI system, various muscles, the heart, glands (e.g., for releasing hormones), etc. IMD 202 generally includes timing and control circuitry 224 and an operating system that may employ microprocessor 226 or a digital state machine for timing sensing and therapy delivery functions and controlling other device functions in accordance with a programmed operating mode. Microprocessor 226 and associated memory 228 (e.g. read only memory, random access memory, etc.) are coupled to the various components of IMD 202 via a data/address bus 238. IMD 202 includes therapy delivery module 220 for delivering a therapy, such as an electrical stimulation or drug therapy, under the control of timing and control circuitry 224. Therapy delivery module 220 includes pulse-generating circuitry 222 for generating electrical stimulation pulses (e.g., bursts of electrical stimulation pulses) under the control of timing and control circuitry 224. As will be described herein, pulse-generating circuitry 222 generates stimulation pulses for stimulating the DRG.

For delivering electrical stimulation pulses, pulse-generating circuitry 222 may be coupled to two or more electrodes 206 via a switch matrix 230. Switch matrix 230 is used for selecting which electrodes and corresponding polarities are used for delivering electrical stimulation pulses. Electrodes 206 may include lead-based electrodes, leadless electrodes incorporated on IMD 202, and/or the IMD housing configured for use as a can or case electrode.

Electrodes 206 may also be used for sensing electrical signals within the body, such as efferent and afferent nerve signals. In other words, the IMD 202 includes monitoring apparatus, which includes electrodes 206 amongst other things. Nerve signals are sensed using any of the electrodes 206 for detecting the electrical activity (e.g., parasympathetic activity, etc.) of various nerves.

Electrodes used for sensing and electrodes used for stimulation may be selected via switch matrix 230. When used for sensing, electrodes 206 are coupled to signal processing circuitry 232 via switch matrix 230. Processing circuitry 232 includes sense amplifiers and may include other signal conditioning circuitry and an analog to digital converter. In other words, the IMD 202 may include a sensing module, e.g., includes switch matrix 230, signal processing circuitry 232, etc. Electrically sensed signals may then be used by microprocessor 226 for detecting physiological events. Further, the microprocessor 226 may have the ability to program amplifiers and other electronic circuits for monitoring neuronal signals (to, e.g., adjust the magnitude of the gain, the filtering, the sampling rate, etc.) and to process raw data for integration, data analysis, and comparison of signals.

The monitoring apparatus of the IMD 202 may further include sensors 242 such as pressure sensors, accelerometers, flow sensors, blood chemistry sensors, activity sensors, and/or other physiological sensors known for use with IMDs. Sensors 242 are coupled to IMD 202 via a sensor interface 234 which provides sensor signals to signal processing circuitry 232. Sensor signals are used by microprocessor 226 for detecting physiological events or conditions. For example, IMD 202 may monitor various physiological parameters (e.g., a patient's creatinine level, a patient's blood urea nitrogen level, a patient's respiration rate, a patient's abdominal fluid content or fluid content in thoracic tissue, pulmonary wedge pressure, etc.). Monitored signals may be used for sensing the need for delivering, adjusting, terminating, and/or initiating therapy under control of the operating system. In other words, the IMD 202 may include a control module, which may include the microprocessor 226 and memory 228 and may be configured using an operating system.

The operating system includes associated memory 228 for storing a variety of programmed-in operating mode and parameter values that are used by microprocessor 226. The memory 228 may also be used for storing data compiled from sensed signals and/or relating to device operating history (e.g., abdominal impedance for use in delivering, adjusting, controlling, initiating, and/or terminating therapy) and/or for communicating such data outside of the patient (e.g., using telemetry communication of recorded history on receipt of a retrieval or interrogation instruction).

IMD 202 further includes telemetry circuitry 236 and antenna 244. Programming commands or data are transmitted during uplink or downlink telemetry between IMD telemetry circuitry 236 and external telemetry circuitry included in a programmer or home monitoring unit.

As described, IMD 202 is able to monitor and analyze various physical parameters to determine the state of an organ, such as a kidney. In response to one or more parameters indicating a state in need of correction, IMD 202 autonomously stimulates at least one electrode positioned at the respective DRG for that organ.

The methods described herein may be implemented by various devices (e.g., implantable medical devices) and systems. Such devices and systems may include one or more leads, electronic circuits, power sources, sensors, electrodes, fluid delivery devices, etc. Further, such devices and systems may be configured to monitor one or more physiological parameters of a patient, e.g., electrical activity of a patient's nervous system, chemical activity of a patient's various organs, chemical activity or pressure levels of a patient's gastrointestinal (GI) system, chemical activity or pressure levels of a patient's renal system, hemodynamic activity of a patient's heart, and electrical activity of a patient's muscles.

The electrical activity of the patient's nerves may include one or more signals and may be monitored (e.g., using electrodes) from locations in or around one or more of the patient's dorsal root ganglions. Such signals may include parasympathetic and/or sympathetic signals propagating along efferent and afferent nerve fibers.

While the electrodes and corresponding processing device are described above as being implantable, one or more components of the system may be external to the patient. For example, the electrodes may be provided in a patch that is placed or secured proximate a patient's skin over the region where the dorsal root ganglion(s) to be stimulated are located. External electrodes, e.g., patches, may be utilized in an emergency situation to influence an organ, such as a kidney. In addition, the processing housing 202 may also be located external to a patient's body and coupled via leads, or wirelessly, to the electrodes.

The stimulation device 202 along with leads 204 and electrodes 206 may be used for one or both of steady state stimulation to mimic daily medication intake (e.g., diuretics) and maximal stimulation to mitigate an acute clinical congestive state. This is done by activating the appropriate renal nerves (e.g., afferent nerves) to mimic their activation signals in the T10-L1 DRGs.

Neuronal fibers that run through the T10-L1 DRGs are mainly C-fibers. Stimulation of the afferent neurons utilize settings to ensure that the electrical stimulation will not stimulate other targets. For example, the stimulation waves may have a tonic form as a relatively high percentage (e.g., 48%) of the renal afferent neurons are tonic, which is characteristic for renal nerves. The tonic stimulation involves low frequencies (e.g., 20-120 Hz range) where amplitude is adjusted for a therapeutic window of stimulation bounded for an individual patient by a perception threshold (e.g., amplitude first detected by the patient) and a discomfort threshold (e.g., amplitude where paresthesia transitions from pleasant to noxious).

The electrical stimulation delivered to the DRG may be delivered at a wide variety of different parameters or settings. Such parameters may include daily timing (e.g., the DRG stimulation may be delivered for a selected time period), sinusoidal current (e.g., 0.05-0.4 mA), amplitude (e.g., within a range of about 0.1-4 V and about 15 Hz), frequency of the pulses (e.g., within a range of about 1 hertz to about 50 hertz), synchronization (e.g., with multiple leads or electrodes), pulse width of each pulse of about 210 microseconds (e.g., within a range of about 100 microseconds to about 1,000 microseconds), and an on/off cycle to prevent battery drain and account for a wearing off time, etc.

When DRG stimulation is used to treat hypertension, the stimulation parameters may at least start with the following settings and be adjusted as needed. Both positive and negative electrodes may be used, and the electrodes may be guided by x-ray or ultrasound guidance to enter the DRG location at T10-L1. The parameters may include amplitude (e.g., within a range of about 0-1 V, e.g., starting at 0.15V depending on skeletal muscle stimulation), frequency of the pulses (e.g., within a range of about 10 hertz to about 20 hertz, e.g., starting at 15 Hz), tonic or burst stimulation, pulse width of each pulse (e.g., within a range of about 200 microseconds to about 1,000 microseconds, e.g., starting at 210 microseconds), and uni- or bi-lateral stimulation, e.g., starting on both sides of the spinal cord. An on/off cycle is used to prevent battery drain and account for a wearing off time as well as to maintain the therapy effect over time. The on/off cycle is varied and improved to sustain the effectiveness of the treatment by preventing adaptation by the nerve ending receptors.

Figure 4:
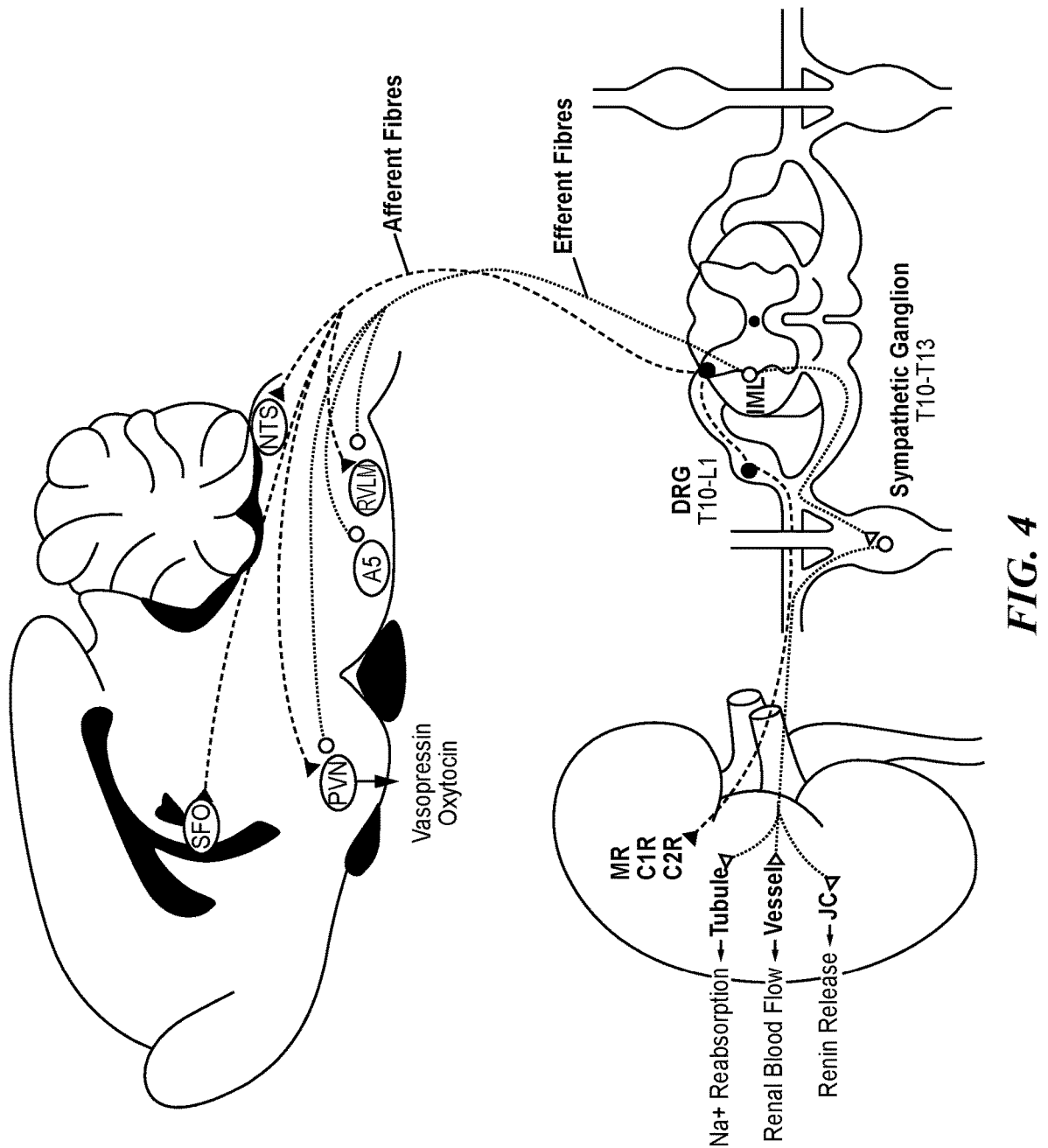
FIG. 4 is a schematic diagram of the anatomical pathways of renal efferent and afferent neurons.

The electrodes delivering DRG stimulation are positioned proximate at least one DRG to activate renal nerve fibers (e.g., afferent nerve fibers) as shown in FIG. 4. Afferent neuron stimulation in the DRG leads to efferent neuron inhibition and subsequently to increased diuresis and lowered blood volume. Renal afferent neurons alone, travel through the DRG at the T10-L1 level. Therefore, when using DRG stimulation to influence kidney function, the electrodes and stimulation are targeted at the DRG proximate the T10-L1 position of the spine.

Figure 5:
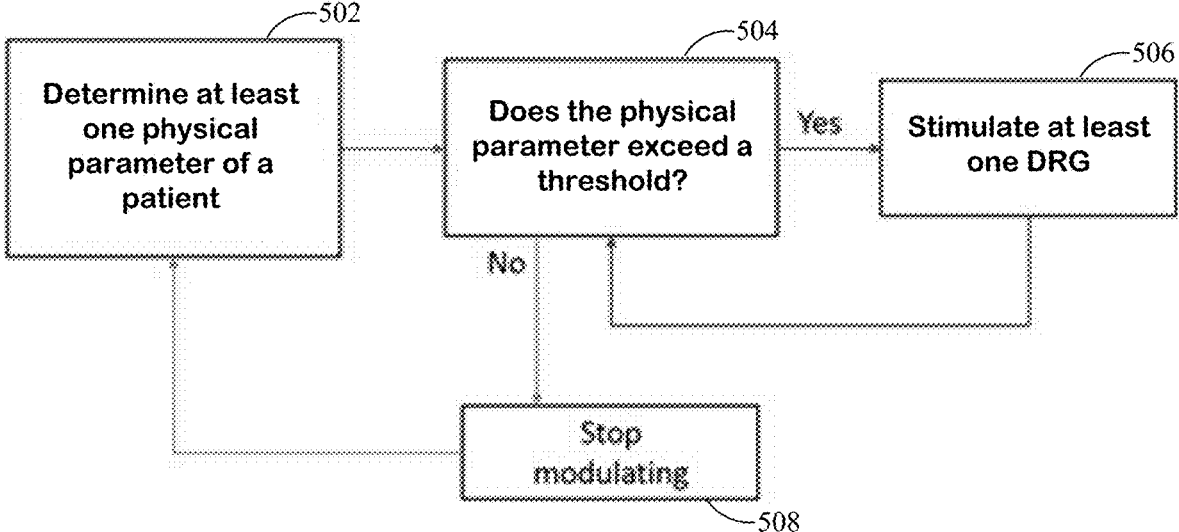
FIG. 5 is a diagram illustrating an exemplary method of DRG stimulation in response to one or more physical parameters.

Turning to FIG. 5, an exemplary method for providing DRG stimulation to influence organ functionality is illustrated. At least one physical parameter of a patient is measured 502. This could include one, two, or more physical parameters such as a patient's creatinine level, a patient's blood urea nitrogen level, a patient's respiration rate, a patient's abdominal fluid content, impedance in various regions of the body, ratios of impedance between body regions, pulmonary capillary wedge pressure, and rates of change thereof. One or more of the physical parameter values is compared with a selected threshold value 504 that represents a point at which either DRG stimulation for a patient should be started, or in the case of ongoing DRG therapy, the DRG stimulation should be adjusted.

If one or more of the physical parameters do not exceed a threshold, modulation is stopped 508. In this context, the term exceed means to go beyond the limits of, which in certain embodiments, may mean to increase above, or decrease below a threshold value. In certain embodiments, if a single parameter does not exceed a predetermined threshold, modulation may be stopped. In other embodiments where two or more parameters are determined, modulation may be stopped if only one, only two, only certain designated, or all parameters do not exceed one or more predetermined levels. The predetermined threshold may be determined for a designated demographic or personalized for each patient. For example, the selected threshold and/or parameters may be determined through a self-learning algorithm to improve, or optimize, conditions for initiating or altering DRG stimulation based on a subset of non-overlapping parameters. In certain embodiments one parameter (e.g., impedance) may inform how/when to stimulate based on a blood urea nitrogen level, or vice versa. If it is determined that DRG stimulation does not need to be adjusted or started based on the comparison to selected threshold values, the method may return to measuring one or more physical parameters 502.

If the comparison to selected threshold values determines that DRG stimulation needs to be started or adjusted (e.g., physical parameter equals or exceeds a selected threshold value), DRG stimulation is initiated (or adjusted) 506. As discussed previously, DRG stimulation may involve stimulating one DRG or multiple DRGs at one or more levels of a patient's spine. In certain embodiments, if a single parameter exceeds a predetermined threshold, the DRG is stimulated. In other embodiments where two or more parameters are determined, stimulation is initiated if only one, only two, only certain designated, or all parameters exceed one or more predetermined levels. Stimulation is continued until one or more designated physical parameters no longer exceed the predetermined threshold(s). In certain embodiments the same physical parameter is used to initiated and halt DRG stimulation, and in other embodiments, different physical parameters may be used to start stimulation than are used to stop stimulation.

In an example embodiment, a single physical parameter such as a patient's blood urea nitrogen (BUN) level may be measured and used to control DRG stimulation. The BUN level indicates the amount of nitrogen which originated from urine and is now present in the blood. BUN levels are measured in blood using a chemical sensor based on a redox reaction. As BUN levels are higher in patients with heart failure, the BUN levels should decrease if diuresis increases and the BUN level can represent a level of diuresis. Thus, when a patient's BUN level is determined to be higher than a selected threshold, DRG stimulation is initiated at the T10-L1 region to activate renal afferent and/or other nerves innervating at least one of the patient's kidneys to increase diuresis as part of the reno-renal reflex. When the patient's BUN level no longer exceeds the selected threshold, DRG stimulation is stopped.

In another example embodiment, two physical parameters are used together such as a patient's BUN level and thoracic fluid content shift. A patient's thoracic fluid content shift can identify a measurement of a patient's abdominal impedance as well as an indirect measurement of a patient's subcutaneous impedance. For example, a patient's intra-abdominal pressure (IAP) is measured to provide an estimate of the amount of splanchic bed overload, which at a certain point can develop a sudden decrease of capacitance and thus acute decompensated heart failure. The IAP is determined by measuring the impedance of the abdominal region to represent congestion. Alternatively, the impedance of the lungs may be measured. Impedance can be measured using a technique disclosed in U.S. Patent Publication No. 2018/0126172, which is incorporated herein by reference. The impedance measurement is used to predict the amount of fluid that needs to be removed in acute heart failure syndromes like congestive heart failure.

The implantable device 202 is used to measure and/or monitor both the BUN levels and the impedance of the patient's abdominal region. Alternatively, the BUN level may be measured offline by another technique. If the BUN level exceeds a selected threshold in combination with high impedance (e.g., impedance also exceeds a selected threshold), DRG stimulation is initiated at the T10-L1 region to induce diuresis and remove fluid from the body. In certain embodiments, if the BUN level exceeds the selected threshold, but the impedance, or thoracic fluid shift, has not, DRG stimulation is not initiated. In other embodiments, if the BUN level exceeds the selected threshold, but the impedance, or thoracic fluid shift, has not, DRG stimulation is initiated.

In certain embodiments, the BUN level and thoracic fluid shift measurements are recorded regularly, e.g., every five minutes, with a lower frequency during a time a patient is deemed to be sleeping, e.g., every hour. In addition, the timing and frequency of measurements can be adjusted in accordance with a patient's body position, physical activity, heart rate, or respiration measured with an on-board sensor. A patient's body position can influence the efficacy of the treatment, and taking into account a patient's body position and activity level allows the device to decrease the frequency of measurements or alter the timing of treatment, so as not to inconvenience the patient.

While certain embodiments are described with respect to influencing kidney function to increase diuresis to treat acute decompensated heart failure and/or hypertension, the sensory fibers of the DRG can be stimulated at any region to influence other organ functionality. For example, the methods described herein may be applicable to kidney dialysis, preventing or mitigating renal failure caused by diabetes, kidney diseases and/or heart failure, and treating COVID-19. The methods provide treatment using the lower current of DRG stimulation alone, without a need for medication.

ILLUSTRATIVE EMBODIMENTS

The technology described herein is defined in the claims. However, below is provided a non-exhaustive listing of non-limiting embodiments. Any one or more of the features of these embodiments may be combined with any one or more features of another example, embodiment, or aspect described herein.

In illustrative Embodiment A1, a system comprises at least one electrode and computing apparatus comprising one or more processors and operably coupled to the at least one electrode. The at least one electrode delivers electrical stimulation to a patient's dorsal root ganglion (DRG) to activate renal afferent and/or other nerves innervating at least one of the patient's kidneys. The computing apparatus is configured to control the electrical stimulation delivered by the at least one electrode to the DRG to inhibit activation of renal efferent nerves innervating the at least one of the patient's kidneys to promote diuresis. In illustrative Embodiment A2, a system comprises the system of Embodiment A1 wherein the at least one electrode is configured to deliver electrical stimulation to at least one of the left and right DRG of at least one of the T10 to L1 vertebrae of the patient to activate renal afferent nerves innervating at least one of the patient's kidneys. In illustrative Embodiment A3, a system comprises the system of any one of the preceding Embodiments wherein the at least one electrode is configured to deliver electrical stimulation to the left and right DRG of at least one of the T10 to L1 vertebrae of the patient to activate renal afferent nerves innervating at least one of the patient's kidneys.

In illustrative Embodiment A4, a system comprises the system of any one of the preceding Embodiments and comprises at least two electrodes to deliver electrical stimulation to at least one of the left and right DRG of at least one of the T10 to L1 vertebrae of the patient to activate renal afferent nerves innervating at least one of the patient's kidneys. In illustrative Embodiment A5, a system comprises the system of any one of the preceding Embodiments and comprises at least two electrodes to deliver electrical stimulation to the left and right DRG of at least one of the T10 to L1 vertebrae of the patient to activate renal afferent nerves innervating both of the patient's kidneys.

In illustrative Embodiment A6, a system comprises the system of any one of the preceding Embodiments wherein the at least one electrode is an external electrode to be positioned external to the patient's body. In illustrative Embodiment A7, a system comprises the system of Embodiment A6 wherein the at least one electrode is integrated in a patch configured to be positioned near at least one of the patient's DRG of at least one of the T10 to L1 vertebrae to stimulate at least one the left and right DRG. In illustrative Embodiment A8, a system comprises the system of any one of the preceding Embodiments wherein at least one electrode is an implantable electrode to be implanted in the patient's body.

In illustrative Embodiment A9, a system comprises the system of any one of the preceding Embodiments wherein controlling the electrical stimulation delivered by the at least one electrode to the DRG comprises controlling the electrical stimulation to be delivered to the DRG according to a predetermined schedule.

In illustrative Embodiment A10, a system comprises the system of any one of the preceding Embodiments wherein controlling the electrical stimulation delivered by the at least one electrode to the DRG comprises controlling the electrical stimulation to be delivered to the DRG based on an activity sensor.

In illustrative Embodiment A11, a system comprises the system of any one of the preceding Embodiments wherein controlling the electrical stimulation delivered by the at least one electrode to the DRG comprises controlling the electrical stimulation to be delivered to the DRG based on a sensed position of the patient's body.

In illustrative Embodiment A12, a system comprises the system of any one of the preceding Embodiments comprising at least one sensor to detect at least one physiological parameter of the patient, wherein the computing apparatus is operably coupled to the at least one sensor, and wherein controlling the electrical stimulation delivered by the at least one electrode to the DRG comprises controlling the electrical stimulation delivered to the DRG by the at least one electrode in response to the detected physiological parameter. In illustrative Embodiment A13, a system comprises the system of Embodiment A12 wherein the at least one physiological parameter of the patient includes at least one of a patient's creatinine level, a patient's blood urea nitrogen level, a patient's respiration rate, a patient's abdominal fluid content, a patient's thoracic fluid content, and a patient's capillary wedge pressure. In illustrative Embodiment A14, a system comprises the system of Embodiment A13 wherein a rate of change is determined for the at least one physiological parameter and electrical stimulation is controlled in response to the rate of change passing a predetermined, individualized threshold.

In illustrative Embodiment A15, a system comprises the system of any one of Embodiments A12 through A14 wherein the electrical stimulation delivered to the DRG by the at least one electrode is increased if the sensed at least one physiological parameter is equal to or greater than a threshold. In illustrative Embodiment A16, a system comprises the system of any one of Embodiments A12 through A15 wherein the at least one physiological parameter comprises thoracic fluid content shift. In illustrative Embodiment A17, a system comprises the system of any one of Embodiments A12 through A15 wherein the at least one physiological parameter is the patient's blood urea nitrogen concentration.

In illustrative Embodiment A18, a system comprises the system of any one of the Embodiments A12 through A17 and comprises a plurality of sensors, wherein a first sensor is configured to detect a first physiological parameter and a second sensor is configured to detect a second physiological parameter and the computing apparatus controls the electrical stimulation delivered by the at least one electrode in response to at least one of the detected first and second parameters meeting or exceeding a threshold. In illustrative Embodiment A19, a system comprises the system of Embodiment A18 wherein the computing apparatus controls the electrical stimulation delivered by the at least one electrode in response to a combination of the detected parameters meeting or exceeding a threshold. In illustrative Embodiment A20, a system comprises the system of any one of the preceding Embodiments wherein the combination of parameters provide input to a self-learning algorithm to determine a threshold to initiate stimulating based on a subset of additional parameters. In illustrative Embodiment A21, a system comprises the system of Embodiment A19 wherein the first physiological parameter is the patient's blood urea nitrogen concentration and the second physiological parameter is the patient's abdominal impedance.

In illustrative Embodiment A22, a system comprises the system of any one of the preceding Embodiments wherein the computing apparatus is configured to adjust one or more parameters of the electrical stimulation delivered to the DRG by the at least one electrode, wherein the one or more parameters comprise one or more of pulse width, amplitude, frequency, and on/off cycle timing.

In illustrative Embodiment B1, a system comprises at least one electrode and computing apparatus comprising one or more processors and operably coupled to the at least one electrode. The electrode delivers electrical stimulation to a patient's dorsal root ganglion (DRG) to activate afferent nerves innervating at least one of the patient's organs, and the computing apparatus is configured to control the electrical stimulation delivered by the at least one electrode to the DRG to inhibit efferent nerves innervating the at least one of the patient's organs.

In illustrative Embodiment B2, a system comprises the system of Embodiment B1 wherein controlling the electrical stimulation delivered by the at least one electrode to the DRG comprises controlling the electrical stimulation to be delivered to the DRG according to a predetermined schedule.

In illustrative Embodiment B3, a system comprises the system of Embodiment B1 and further comprises at least one sensor to detect at least one physiological parameter of the patient, wherein the computing apparatus is operably coupled to the at least one sensor, and wherein controlling the electrical stimulation delivered by the at least one electrode to the DRG comprises controlling the electrical stimulation delivered to the DRG by the at least one electrode in response to the detected physiological parameter. In illustrative Embodiment B4, a system comprises the system of Embodiment B3 wherein a rate of change is determined for the at least one physiological parameter and electrical stimulation is controlled in response to the rate of change passing a predetermined, individualized threshold. In illustrative Embodiment B5, a system comprises the system of any one of the Embodiments B1 through B4 wherein the computing apparatus is configured to adjust one or more parameters of the electrical stimulation delivered to the DRG by the at least one electrode, wherein the one or more parameters comprise one or more of pulse width, amplitude, frequency, and on/off cycle timing.

In illustrative Embodiment C, a method comprises determining at least one physical parameter of a patient and comparing the at least one physical parameter with a selected threshold for the parameter. When the physical parameter meets or exceeds the selected threshold, a dorsal root ganglion of the patient is stimulated to influence at least one function of an organ of the patient.

The methods described herein are intended to illustrate the general functional operation of the devices and/or systems described herein, and should not be construed as reflective of a specific form of software or hardware necessary to practice one or more of the methods described herein. It is believed that the particular form of software will be determined primarily by the particular system architecture employed in a device (e.g., an implantable medical device) and/or system and by the particular detection and therapy delivery methodologies employed by the device and/or system. Providing software to accomplish the described methods in the context of any modern implantable medical device, given the disclosure herein, is within the abilities of one of skill in the art.

Further, methods described in conjunction with flow charts presented herein may be implemented in a computer-readable medium that includes computer instructions or software for causing a programmable processor to carry out the methods described. Computer instructions are typically stored in a "computer-readable medium" such as random access memory (RAM). "Computer-readable medium" includes but is not limited to any volatile or non-volatile media, such as a RAM, read only memory (ROM), non-volatile random access memory (NVRAM), electrically erasable programmable read-only memory (EEPROM), compact disc read-only memory (CD-ROM)), flash memory, and the like. The instructions may be implemented as one or more software modules, which may be executed by themselves or in combination with other software.

The hardware used to the accomplish the described methods, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions and processes described herein may be embodied as software, firmware, hardware, or any combination thereof. As used herein, the term "circuitry" may be implemented in software as executed by one or more processes, firmware, hardware, or any combination thereof.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any range within that range.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A system comprising:
at least one electrode to deliver electrical stimulation to a patient's dorsal root ganglion (DRG) to activate renal afferent and/or other nerves innervating at least one of the patient's kidneys;
computing apparatus comprising one or more processors and operably coupled to the at least one electrode and configured to control the electrical stimulation delivered by the at least one electrode to the DRG to inhibit activation of renal efferent nerves innervating the at least one of the patient's kidneys to promote diuresis; and
at least one sensor to detect at least one physiological parameter of the patient, wherein the computing apparatus is operably coupled to the at least one sensor, and wherein controlling the electrical stimulation delivered by the at least one electrode to the DRG comprises controlling the electrical stimulation delivered to the DRG by the at least one electrode in response to the detected physiological parameter;
wherein the at least one physiological parameter of the patient includes at least one of a patient's creatinine level, a patient's blood urea nitrogen level, a patient's respiration rate, a patient's abdominal fluid content, a patient's thoracic fluid content, and a patient's capillary wedge pressure;
wherein a rate of change is determined for the at least one physiological parameter and electrical stimulation is controlled in response to the rate of change passing a predetermined, individualized threshold.

2. The system of claim 1, wherein the at least one electrode is configured to deliver electrical stimulation to at least one of the left and right DRG of at least one of the T10 to L1 vertebrae of the patient to activate renal afferent nerves innervating at least one of the patient's kidneys.

3. The system of claim 1, wherein the at least one electrode is configured to deliver electrical stimulation to the left and right DRG of at least one of the T10 to L1 vertebrae of the patient to activate renal afferent nerves innervating at least one of the patient's kidneys.

4. The system of claim 1, comprising at least two electrodes to deliver electrical stimulation to at least one of the left and right DRG of at least one of the T10 to L1 vertebrae of the patient to activate renal afferent nerves innervating at least one of the patient's kidneys.

5. The system of claim 1, comprising at least two electrodes to deliver electrical stimulation to the left and right DRG of at least one of the T10 to L1 vertebrae of the patient to activate renal afferent nerves innervating both of the patient's kidneys.

6. The system of claim 1, wherein the at least one electrode is an external electrode to be positioned external to the patient's body.

7. The system of claim 6, wherein the at least one electrode is integrated in a patch configured to be secured to the patient's skin and positioned near at least one of the patient's DRG of at least one of the T10 to L1 vertebrae to stimulate at least one the left and right DRG.

8. The system of claim 1, wherein at least one electrode is an implantable electrode to be implanted in the patient's body.

9. The system of claim 1, wherein controlling the electrical stimulation delivered by the at least one electrode to the DRG comprises controlling the electrical stimulation to be delivered to the DRG according to a predetermined schedule.

10. The system of claim 1, wherein controlling the electrical stimulation delivered by the at least one electrode to the DRG comprises controlling the electrical stimulation to be delivered to the DRG based on an activity sensor.

11. The system of claim 1, wherein controlling the electrical stimulation delivered by the at least one electrode to the DRG comprises controlling the electrical stimulation to be delivered to the DRG based on a sensed position of the patient's body.

12. The system of claim 1, wherein the electrical stimulation delivered to the DRG by the at least one electrode is increased if the sensed at least one physiological parameter is equal to or greater than a threshold.

13. The system of claim 1, wherein the at least one physiological parameter comprises thoracic fluid content shift.

14. The system of claim 1, wherein the at least one physiological parameter is the patient's blood urea nitrogen concentration.

15. The system of claim 1, comprising a plurality of sensors, wherein a first sensor is configured to detect a first physiological parameter and a second sensor is configured to detect a second physiological parameter and the computing apparatus controls the electrical stimulation delivered by the at least one electrode in response to at least one of the detected first and second parameters meeting or exceeding a threshold.

16. The system of claim 15, wherein the computing apparatus controls the electrical stimulation delivered by the at least one electrode in response to a combination of the detected parameters meeting or exceeding a threshold.

17. The system of claim 16, wherein the combination of parameters provide input to a self-learning algorithm to determine a threshold to initiate stimulating based on a subset of additional parameters.

18. The system of claim 16, wherein the first physiological parameter is the patient's blood urea nitrogen concentration and the second physiological parameter is the patient's abdominal impedance.

19. The system of claim 1, wherein the computing apparatus is configured to adjust one or more parameters of the electrical stimulation delivered to the DRG by the at least one electrode, wherein the one or more parameters comprise one or more of pulse width, amplitude, frequency, and on/off cycle timing.

20. A system comprising:

at least one electrode to deliver electrical stimulation to a patient's dorsal root ganglion (DRG) to activate afferent nerves innervating at least one of the patient's organs;

computing apparatus comprising one or more processors and operably coupled to the at least one electrode and configured to control the electrical stimulation delivered by the at least one electrode to the DRG to inhibit efferent nerves innervating the at least one of the patient's organs; and at least one sensor to detect at least one physiological parameter of the patient, wherein the computing apparatus is operably coupled to the at least one sensor, and wherein controlling the electrical stimulation delivered by the at least one electrode to the DRG comprises controlling the electrical stimulation delivered to the DRG by the at least one electrode in response to the detected physiological parameter;

wherein the at least one physiological parameter of the patient includes at least one of a patient's creatinine level, a patient's blood urea nitrogen level, a patient's respiration rate, a patient's abdominal fluid content, a patient's thoracic fluid content, and a patient's capillary wedge pressure;

wherein a rate of change is determined for the at least one physiological parameter and electrical stimulation is controlled in response to the rate of change passing a predetermined, individualized threshold.

21. The system of claim 20, wherein controlling the electrical stimulation delivered by the at least one electrode to the DRG comprises controlling the electrical stimulation to be delivered to the DRG according to a predetermined schedule.

22. The system of claim 20, wherein the computing apparatus is configured to adjust one or more parameters of the electrical stimulation delivered to the DRG by the at least one electrode, wherein the one or more parameters comprise one or more of pulse width, amplitude, frequency, and on/off cycle timing.

23. A method comprising:

determining, using at least one sensor, at least one physical parameter of a patient;

determining a rate of change for the at least one physical parameter;

comparing the rate of change for the at least one physical parameter with a selected threshold for the parameter; and when the rate of change for the physical parameter meets or exceeds the selected threshold, stimulating, using at least one electrode, a dorsal root ganglion of the patient to activate renal afferent and/or other nerves innervating at least one of the patient's kidneys;

wherein the at least one physical parameter of the patient includes at least one of a patient's creatinine level, a patient's blood urea nitrogen level, a patient's respiration rate, a patient's abdominal fluid content, a patient's thoracic fluid content, and a patient's capillary wedge pressure.

* * * * *